(12) United States Patent
Yande

(10) Patent No.: US 7,344,510 B1
(45) Date of Patent: Mar. 18, 2008

(54) ORAL HYGIENE DEVICE

(76) Inventor: Chandrakant R. Yande, 6 Bolfmar Ave., West Windsor, NJ (US) 08550

( * ) Notice: Subject to any disclaimer, the term of this patent is extended or adjusted under 35 U.S.C. 154(b) by 0 days.

(21) Appl. No.: 11/689,957

(22) Filed: Mar. 22, 2007

Related U.S. Application Data

(63) Continuation-in-part of application No. 11/531,674, filed on Sep. 13, 2006, now abandoned, which is a continuation of application No. 10/948,024, filed on Sep. 23, 2004, now abandoned.

(51) Int. Cl.
*A61H 13/00* (2006.01)

(52) U.S. Cl. .................. 601/162; 601/155; 601/165; 601/169; 433/80

(58) Field of Classification Search ............... 601/154, 601/155, 162–165, 169; 433/80, 82, 88; 4/615; 401/42, 46, 289; 239/317, 436; 251/149.1, 251/149.5; 285/8, 81, 93, 373, 423
See application file for complete search history.

(56) References Cited

U.S. PATENT DOCUMENTS

| | | | |
|---|---|---|---|
| 3,227,158 A | 1/1966 | Mattingly | |
| 3,542,017 A | 11/1970 | Adams | |
| 3,545,435 A | 12/1970 | Hollander | |
| 3,820,532 A | 6/1974 | Eberhardt et al. | |
| 4,141,352 A | 2/1979 | Ebner et al. | |
| 5,027,798 A * | 7/1991 | Primiano | 601/165 |
| 5,220,914 A * | 6/1993 | Thompson | 601/162 |
| 5,399,089 A | 3/1995 | Eichman et al. | |
| 5,626,472 A * | 5/1997 | Pennetta | 601/165 |
| 6,740,053 B2 | 5/2004 | Kaplowitz | |

\* cited by examiner

*Primary Examiner*—Quang D. Thanh
(74) *Attorney, Agent, or Firm*—Crossley Patent Law; Mark Ashley Crossley

(57) ABSTRACT

An oral hygiene device, which includes a hand-held cylindrical device having a controllable dial and water-emitting nipple created by water pressure is disclosed. The oral hygiene device includes a cylindrical body which is hand-held, a control dial, having a valve, mounted onto the body; a nipple mounted at its proximal end to the body, the nipple having a slit on its distal end and being interchangeable; a conduit mounted between the body and an open-shutoff valve; and an open-shutoff valve mounted between the conduit and a connector body mounted to a water source. The device cleanses and dislodges food particles from teeth and massages the gums.

8 Claims, 12 Drawing Sheets

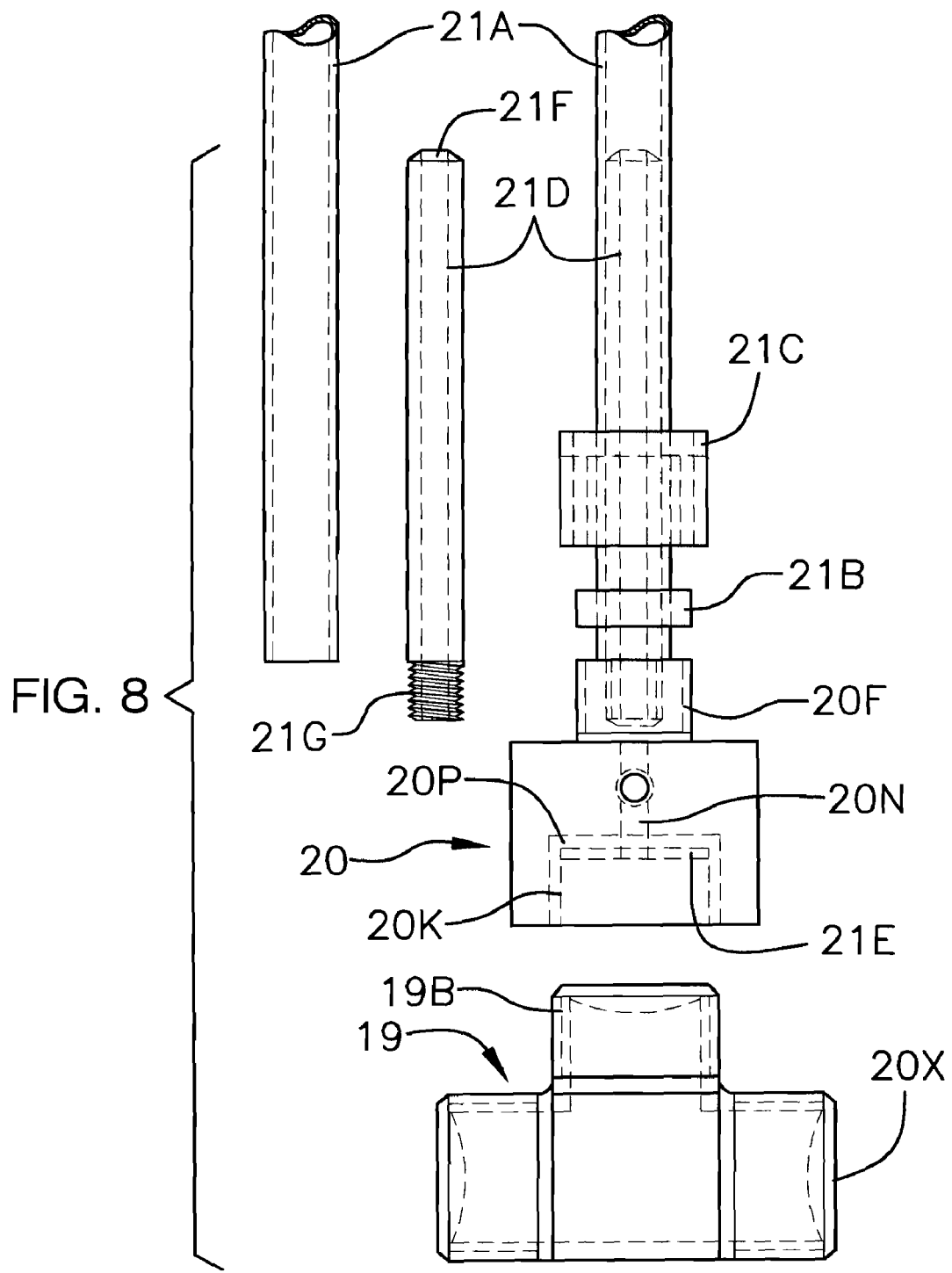

ORAL HYGIENE DEVICE

CROSS-REFERENCE TO RELATED APPLICATIONS

Continuation-in-Part of U.S. application Ser. No. 11/531,674 filed on Sep. 13, 2006 now abandoned, which is a continuation of U.S. application Ser. No. 10/948,024 filed on Sep. 23, 2004 now abandoned.

FEDERALLY SPONSORED RESEARCH OR DEVELOPMENT

Not Applicable

INCORPORATION BY REFERENCE OF MATERIAL SUBMITTED ON A COMPACT DISK

Not Applicable

SPECIFICATION

TO ALL WHOM IT MAY CONCERN

Be it known that I, Chandrakant R. Yande, a citizen of the United States, have invented new and useful improvements in an oral hygiene device as described in this specification. This application claims the benefit of my previously filed United States Provisional Application Number 11/531,674, filed on Sep. 13, 2006, which is a continuation of U.S. application Ser. No. 10/948,024 filed on Sep. 23, 2004 now abandoned.

BACKGROUND OF THE INVENTION

This invention relates to dental care and, more particularly, to an oral hygiene device which comprises a hand-held cylindrical device having a controllable dial and pulsating slit nipple created by water pressure. This device cleanses and dislodges food particles from teeth and massages the gums.

DESCRIPTION OF THE PRIOR ART

In the prior art, numerous oral hygiene devices are provided. For example, one patent teaches a device for use with cold-water shutoff valve of the domestic supply line and with cold and hot water shutoff valves, as a combination, of the supply lines under a sink in the bathroom. In addition, many useful patented devices provided water pulsating jets or nozzles for dental hygiene; however, these devices present some issues. In conventional dental hygiene devices, a desirable water pressure is acquired by means of pumps and by means of water energy at the faucet. Many complex situations are applied to achieve the desired results. The use of electricity near by water means invites danger. Currently available devices often provide many short-lived parts which are expensive to replace. Furthermore, the use of presently available devices is often cumbersome. Some of the problems have been partially solved by implementation of improved devices, but these devices continue to encounter significant problems.

For example, U.S. Pat. No. 3,227,158, issued to Mattingly, teaches a pulsed water jet through nozzle under the driving action of an electrically operated pump. The rate of repetition of pulses dislodges food particles and massages the gums.

U.S. Pat. No. 3,542,017, issued to Adams, provides some improvement over other devices and employs a fluid oscillator thereby eliminating shocks. The device creates a pulsating rate to dislodge food particles and to massage the gums.

U.S. Pat. No. 4,141,352, issued to Ebner et al., teaches a liquid reservoir, a jet and a reciprocating piston. The device delivers spurts of liquid through its jet to massage biological tissues of gums and dislodge particles. The oral irrigator operates on electricity.

U.S. Pat. No. 3,820,532, issued to Eberhardt et al., provides a turbine which drives a rotary interrupter to control the speed and a nozzle, which can be moved in various angles. This patent also teaches an additive added to water for use with the device. Similarly, in U.S. Pat. No. 3,545,435, issued to Hollander et al., the water pressure from a faucet is used to turn the turbine and the turbine drives a pump. By adding water pumps to the device, increased water pressure is delivered to a user's mouth.

U.S. Pat. No. 5,399,089, issued to Eichman et al., teaches the concept of priority to the rate of flow of water through the handle of an oral irrigator.

U.S. Pat. No. 6,740,053, issued to Kaplowitz, provides a device mounted to a faucet or a showerhead to deliver a higher volume of water than other devices.

While the above-described devices fulfill their respective and particular objects and requirements, they do not describe an oral hygiene device that provides for the advantages of the present oral hygiene device. In this respect, the present oral hygiene device substantially departs from the conventional concepts and designs of the prior art. Therefore, a need exists for an improved oral hygiene device.

SUMMARY OF THE INVENTION

The present oral hygiene device comprises a novel and improved hand-held cylindrical device having a control dial and an interchangeable, water-powered slit nipple which delivers numerous water pulses for oral irrigation, cleansing and flossing teeth. The present device is simple and is not a complicated mechanism. It is, therefore, an object of the present oral hygiene device to provide an oral irrigator. The present device is powered solely by the applied pressure from a domestic water supply source. The endurance, the powerful slits of water and improved performance are other objects of the present invention.

This invention provides a practical and an endurable solution for massaging biological tissues of gums. Furthermore, the present invention eliminates the use of an electrical pump, a reservoir and a bulky storage of liquid on a sink counter. The device is very practical. It has an instant use and the device is not directly connected to a faucet or a showerhead. Accordingly, like a toothbrush, this device is usable at practically any time of the day or any location. Still another object of the present dental hygiene device invention is that an adult can use the full force of the water pressure coming from the open-shutoff orifice valve and provides a device that children can manage themselves to use the variable force of the hand held device for their individual needs. Accordingly, the present device permits an instant use for water flossing. It permits the directional dial to shut off and open water instantly. It allows children to open and stop the water flow of the hand held device immediately. It permits a user to hold the hand-held device like a toothbrush. The present invention may be connected to a faucet water supply valve under a sink in the bathroom. Accordingly, a clear and complete understanding of the present invention and its usefulness that can be seen from the submitted and accompanying drawings and its supported claims.

Accordingly, a general purpose of the present invention is to provide a novice and better or improved an oral dental hygiene device and to outperform limitations of the known prior arts. Considering the endurance, the powerful water pulses and the performance capabilities of the present oral hygiene device, a further object of the present invention is easy and economic production of said device.

There has thus been outlined, rather broadly, the more important features or an oral hygiene device that the detailed description thereof that follows may be better understood and in order that the present contribution to the art may be better appreciated. There are, of course, additional features of the oral hygiene device that will be described hereinafter and which will form the subject matter of the claims appended hereto.

In this respect, before explaining at least one embodiment of the oral hygiene device in detail, it is to be understood that the oral hygiene device is not limited in its application to the details of construction and to the arrangements of the components set forth in the following description or illustrated in the drawings. The oral hygiene device is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present oral hygiene device. It is important, therefore, that the claims be regarded as including such equivalent constructions insofar as they do not depart from the spirit and scope of the present invention.

It is therefore an object of the present invention to provide an oral hygiene device which has all of the advantages of the prior art and none of the disadvantages.

It is another object of the present invention to provide an oral hygiene device which may be easily and efficiently manufactured and marketed.

It is another object of the present invention to provide an oral hygiene device which is of durable and reliable construction.

It is yet another object of the present invention to provide an oral hygiene device which is economically affordable and available for relevant market segment of the purchasing public.

Other objects, features and advantages of the present invention will become more readily apparent from the following detailed description of the preferred embodiment when considered with the attached drawings and appended claims.

BRIEF DESCRIPTION OF THE DRAWINGS

FIG. 8 is a side elevation view illustrating the open-shutoff orifice valve body attached to a conduit assembly body.

DESCRIPTION OF THE PREFERRED EMBODIMENT

Figure 1:
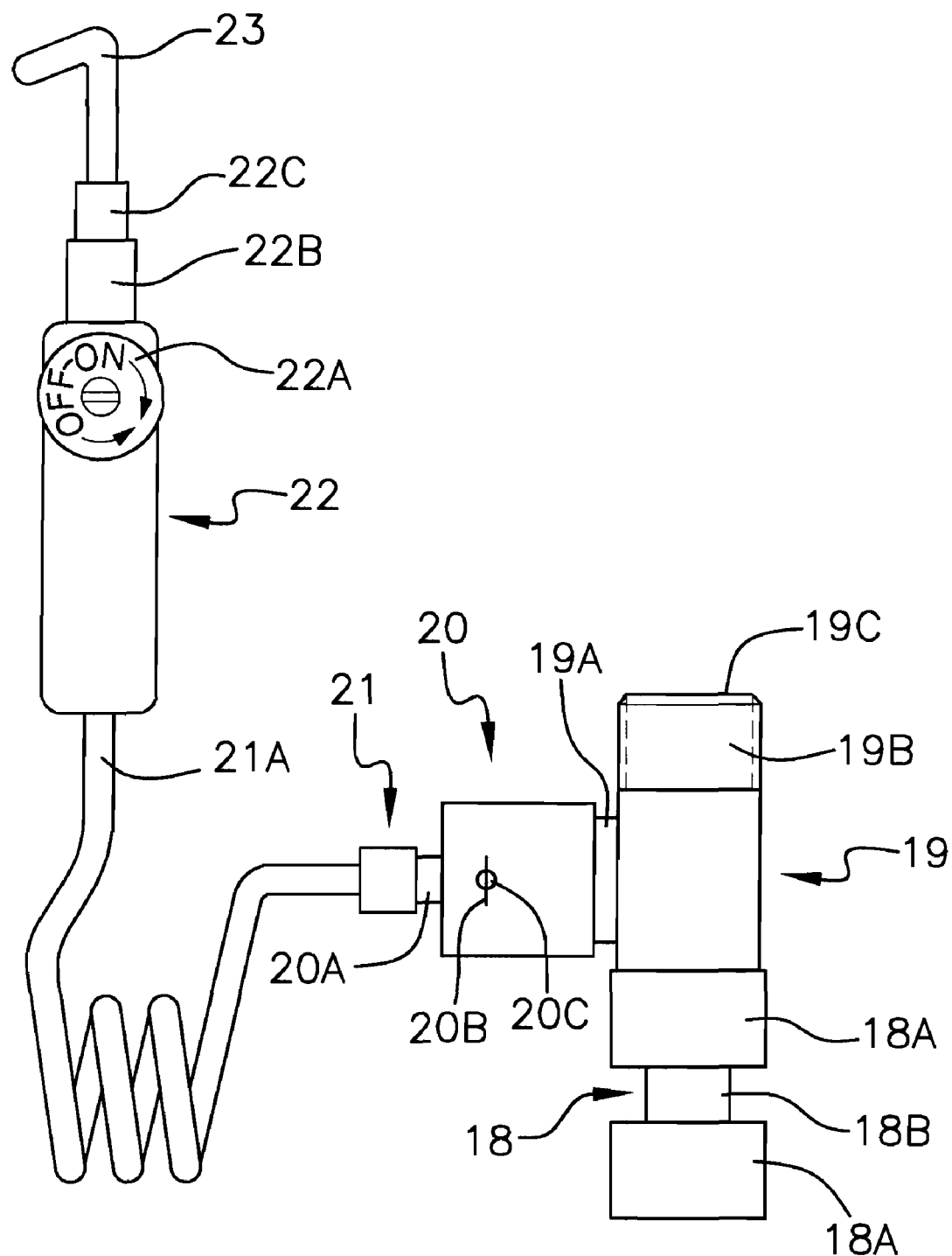
FIG. 1 is a side elevation view of the oral hygiene device.

With reference now to the drawings, and in particular to FIGS. 1 through 12C thereof, a new oral hygiene device embodying the principles and concepts of the present invention and generally designated by the reference numeral 2 will be described.

As best illustrated in FIGS. 1 through 12C, the oral hygiene device 2 is shown. The specific wordings are used in these descriptions for fulfilling the requirements only and it is not to be assumed as a limitation on the present invention.

Figure 2:
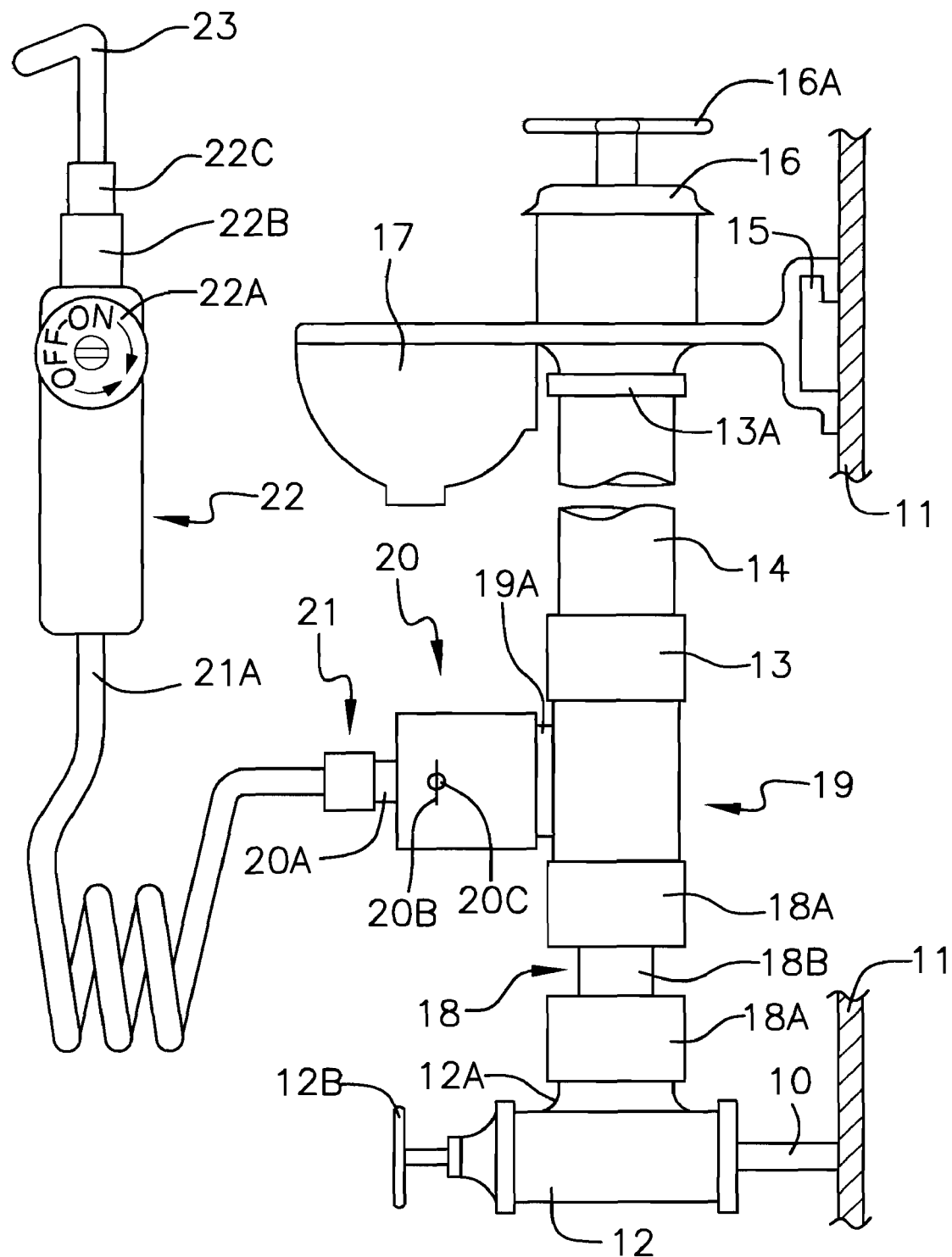
FIG. 2 is a side elevation view of the oral hygiene device as it would appear attached to a domestic water supply line.

Referring to FIGS. 1 and 2 and also to FIGS. 11A, 11B and 12A, 12B, and 12C a bi-functional coupling 18 is connected to a tri-functional connector body 19, while the connector body 19 is connected to an open-shutoff orifice valve body 20. A flexible and inflexible conduit assembly body 21 is connected to the orifice valve body 20. Flexible tubing 21A of the conduit assembly body 21 is connected to a hand-held cylindrical body 22. A directional water pressure control valve 22A is incorporated into the body 22. A nipple 23 and its nipple body 23A are attached to the hand-held cylindrical body 22.

The coupling 18 comprises a central length of tubing 18B with two ends, a first end and a second end, and furthermore, comprises a pair of hexagonal nuts 18A that are attached to each end of the tubing. The connector body 19 essentially comprises three separate necks 19A. Each neck 19A has external male threads 19B and a chamfered end 19C. Furthermore, each neck 19A has an internal bore 19D that allow free flow of water through the connector body 19. All three of the necks 19A are coplanar with one another, with two of the necks 19A being 180 degrees apart from each other and the third neck 19A being 90 degrees from each of the other two necks 19A.

The oral hygiene device 2 can be connected to a wide variety of pressurized water lines. However, it is preferably connected to a domestic water supply line valve 12 of a faucet on a sink for its intended use. Connecting the oral hygiene device 2 to a domestic water supply line 10 is fairly straightforward. First, a handle 12B on a cold water supply line valve 12 is shut off. Then, one needs to disconnect nut 13 of conduit 14 from valve 12. Next, one can reconnect the valve 12 with a nut 18A of coupling 18 and connect the other nut 18A of the coupling 18 to a male threaded end 19B on the connector body 19. Next, one can connect a threaded end 19B of the connector body 19 to nut 13 of the cold water conduit 14. Now, by opening the valve handle 12B, this arrangement reestablishes the water flow to faucet 16 and now, the water under pressure is available to the control valves 20C and 22A.

As can be seen in FIG. 2, the domestic water supply line 10 is connected to valve 12, with the valve having a neck 12A and a handle 12B. The function of the valve 12 is to open and shut off the water supply line 10. A bracket 15 of the sink 17 is attached to wall 11. The sink has a faucet 16, with the faucet 16 having a handle 16A. The nut 13A of the conduit 14 is already connected to the faucet 16.

Figure 3:
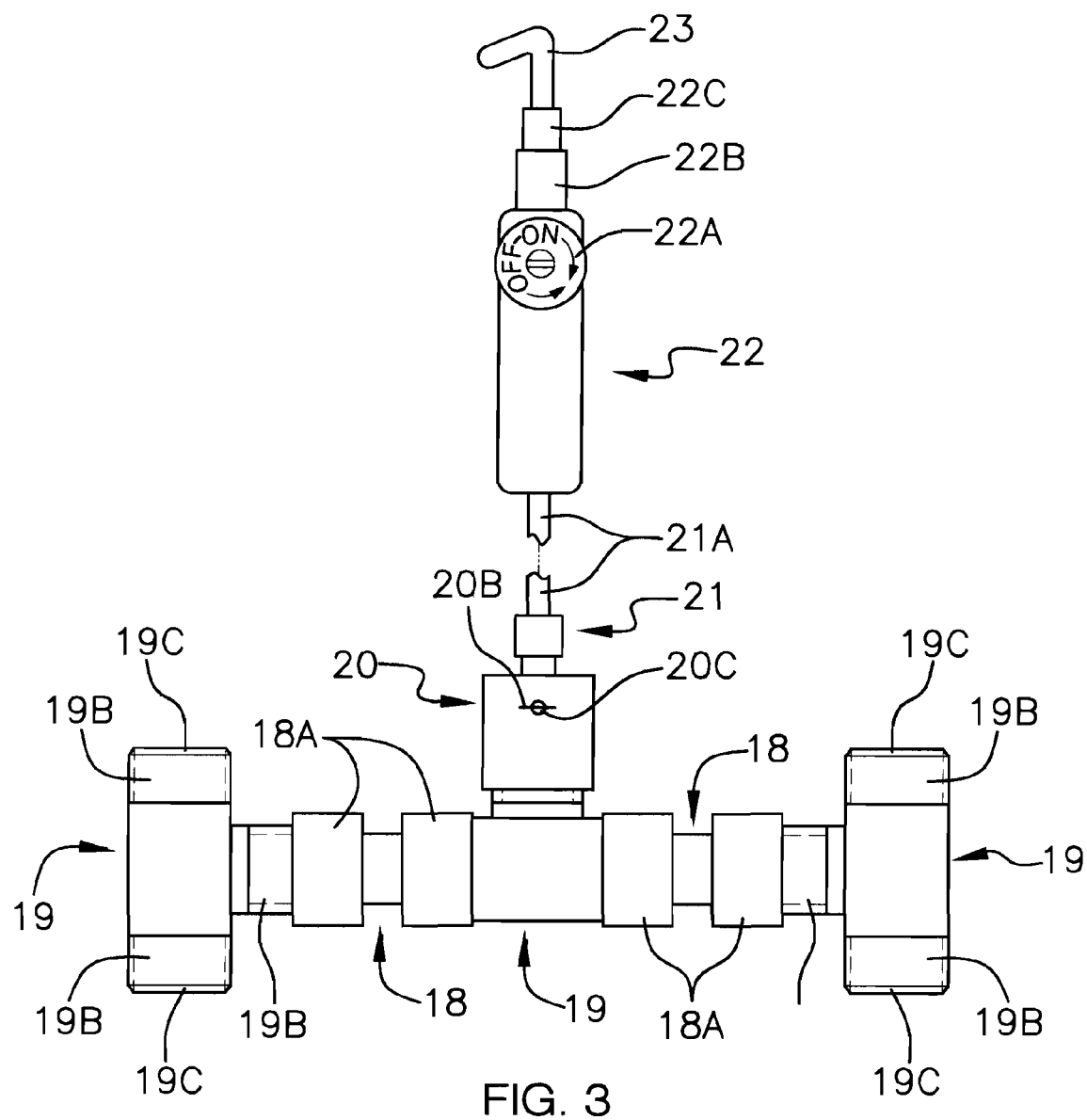
FIG. 3 is a side elevation view of the oral hygiene device as it would appear in a hot and cold water system.

FIG. 3 illustrates the oral hygiene device 2 as it is connected to both hot and cold water lines. In this embodiment, three separate connector bodies 19 are utilized. One of the connector bodies, hereinafter deemed the "central" connector body 19, is connected to an orifice valve body 20 as already shown in FIG. 1. A coupling 18 is attached to each of the other necks 19A of the central connector body 19, with each of these couplings 18 being attached to a connector body 19. The second and third connector bodies 19 used with this embodiment are then connected to the hot and cold water lines, respectively, as further detailed herein.

Figure 4:
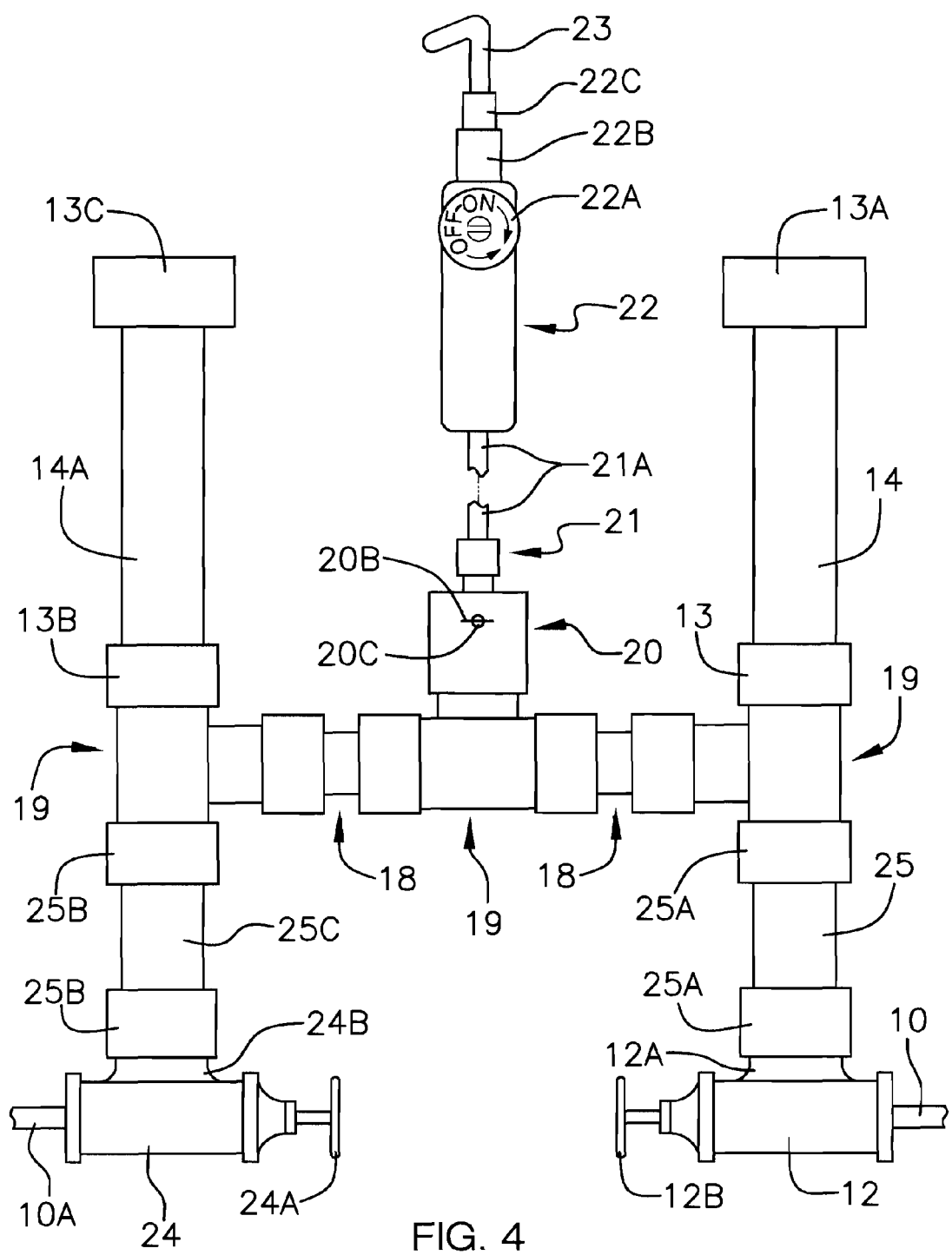
FIG. 4 is a side elevation view of the oral hygiene device as it would appear attached to a hot and cold water supply line system.

FIG. 4 highlights FIG. 3 as it is shown connected to cold and hot water supply line valves 12 and 24, respectively. Accomplishing this task, as before, is mechanically straightforward. First, handles 12B and 24A are to be shut off. Then, one can disconnect nut 13 of the conduit 14 of the cold water from valve 12 and reconnect it to the threaded end 19B of the connector body 19. Similarly, one can disconnect nut 13B of the conduit 14A of the hot water from the valve 24. In order to have the device 2 connected to the supply lines, it needs conduits 25 and 25C with the similar connecting nuts 25A and 25B at the both ends. Between the second and third connector bodies 19 highlighted and described in FIG. 3, one of these can be threadably attached to nut 25A, while the other connector body 19 can be threadably attached to nut 25B. After opening the handles 12B and 24A, respectively, the cold and hot water under pressure is available to the control valve 20C of the orifice valve body 20 and to the control valve 22A of the body 22.

Figure 5A:
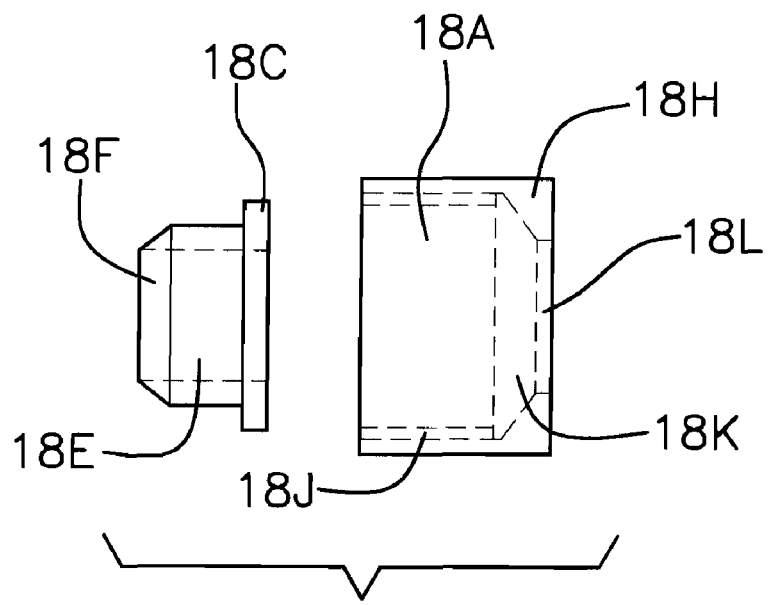
FIG. 5A is a side elevation view of some of the components of a bi-functional coupling before they have been assembled.
Figure 5B:
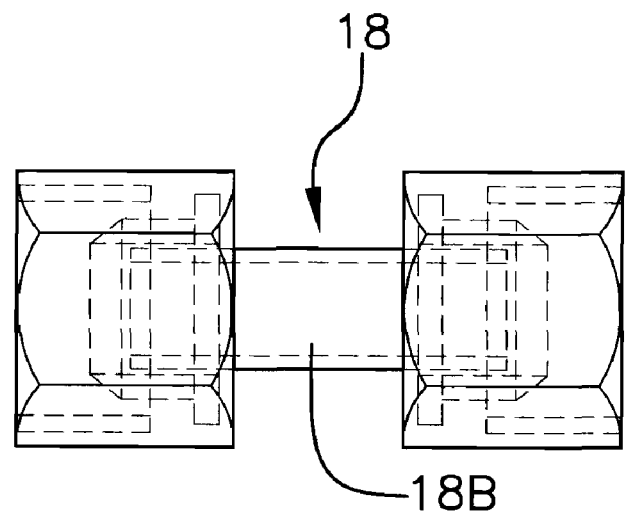
FIG. 5B is a side elevation view of a bi-functional coupling after they have been assembled.

In FIGS. 5A-5B, a coupling 18 is detailed. The function of the coupling 18 is to connect the water shutoff valve 12 and the connector body 19. The coupling 18 is made of two hexagonal or of similar configurational nuts 18A, a length of tubing 18B, and two sleeves 18E. The nuts 18A are threaded in through bore 18L head to head 18H over the tubing 18B. The sleeve 18E slides over the tubing 18B, while collar 18C is inserted first into the nut 18A. Once inserted, the male flare 18F on each nut 18A is arranged to be edge to edge of the tubing 18B so it fits snugly. However, some deviation is clearly permitted. Once the various components of coupling 18 are assembled, the sleeves 18E are then soldered or welded to the tubing 18B. The spacing between the head to head of the nuts 18A should be judged by the free rotation of the nuts 18A over the collar 18C of the sleeves 18E. Another important function of the coupling 18 is that it can be connected to an open-shutoff valves 12 at any angle or at any position. The length of the tubing 18B is to be adjusted accordingly so that the configuration seen in FIG. 3 can be accommodated.

Figure 6A:
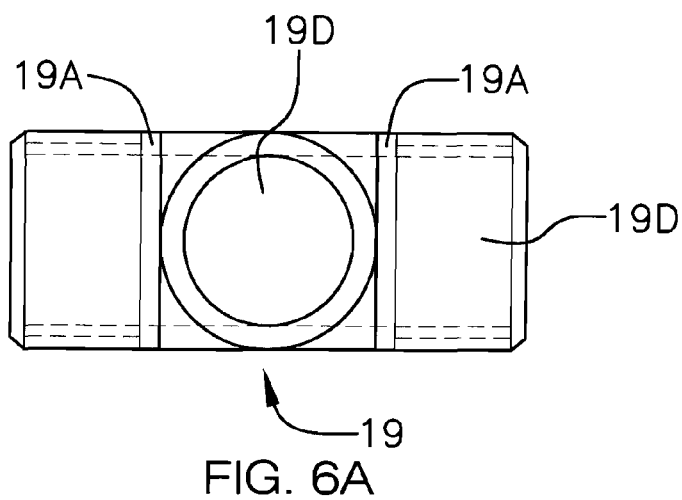
FIG. 6A is a top plan view of a tri-functional connector.
Figures 6B, 6C:
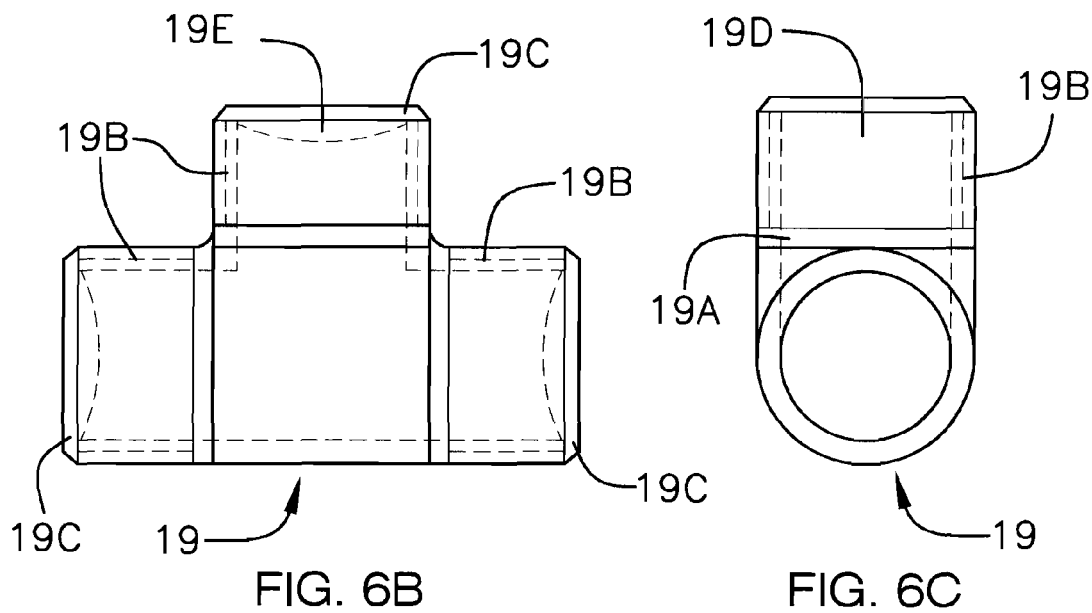
FIG. 6B is a side elevation view of a tri-functional connector.
FIG. 6C is an end view of a tri-functional connector.
Figure 7A:
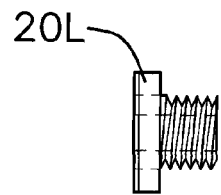
FIG. 7A is a side elevation view of a hex nut used with the open-shutoff orifice valve body.
Figure 7B:
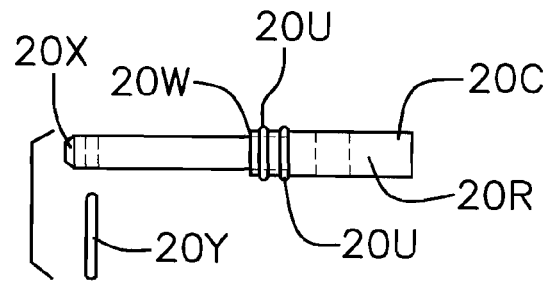
FIG. 7B is a side elevation view of a control valve used with the open-shutoff orifice valve body.
Figure 7D:
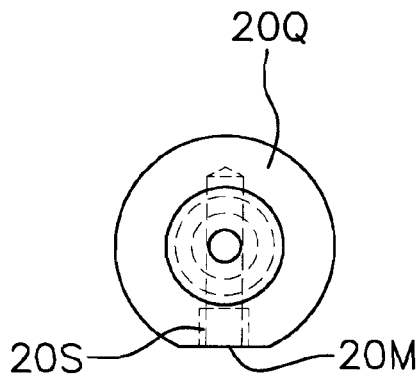
FIG. 7D is a top plan view of the open-shutoff orifice valve body.
Figure 7C:
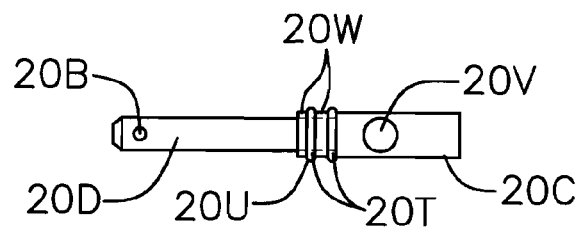
FIG. 7C is a top plan view of a control valve used with the open-shutoff orifice valve body.
Figure 7E:
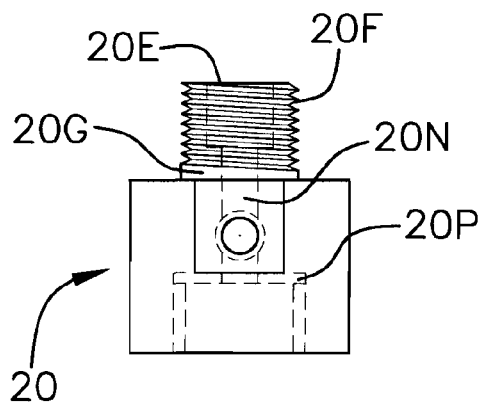
FIG. 7E is a front elevation view of the open-shutoff orifice valve body.
Figure 7F:
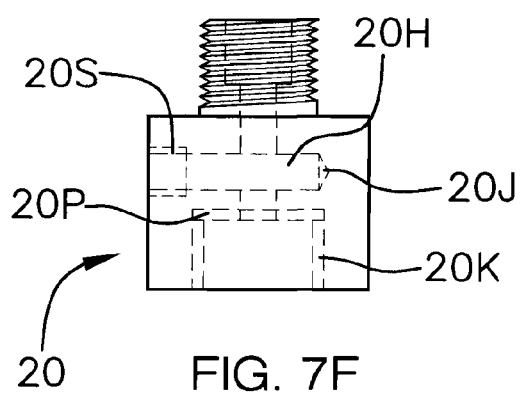
FIG. 7F is a side elevation view of the open-shutoff orifice valve body.
Figure 9A:
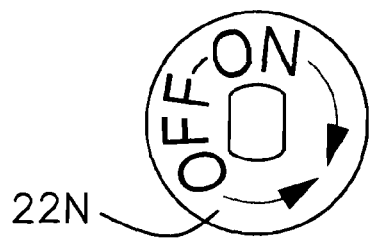
FIG. 9A is a top plan view of a directional dial.
Figure 9B:
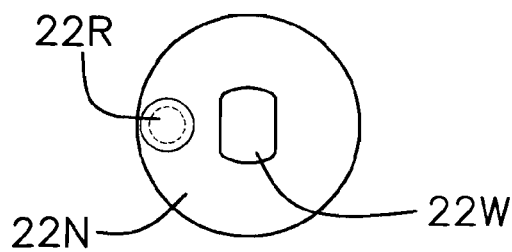
FIG. 9B is a bottom plan view of a directional dial.
Figure 9C:
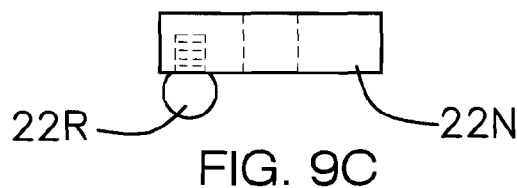
FIG. 9C is a side elevational view of a directional dial.
Figure 9D:
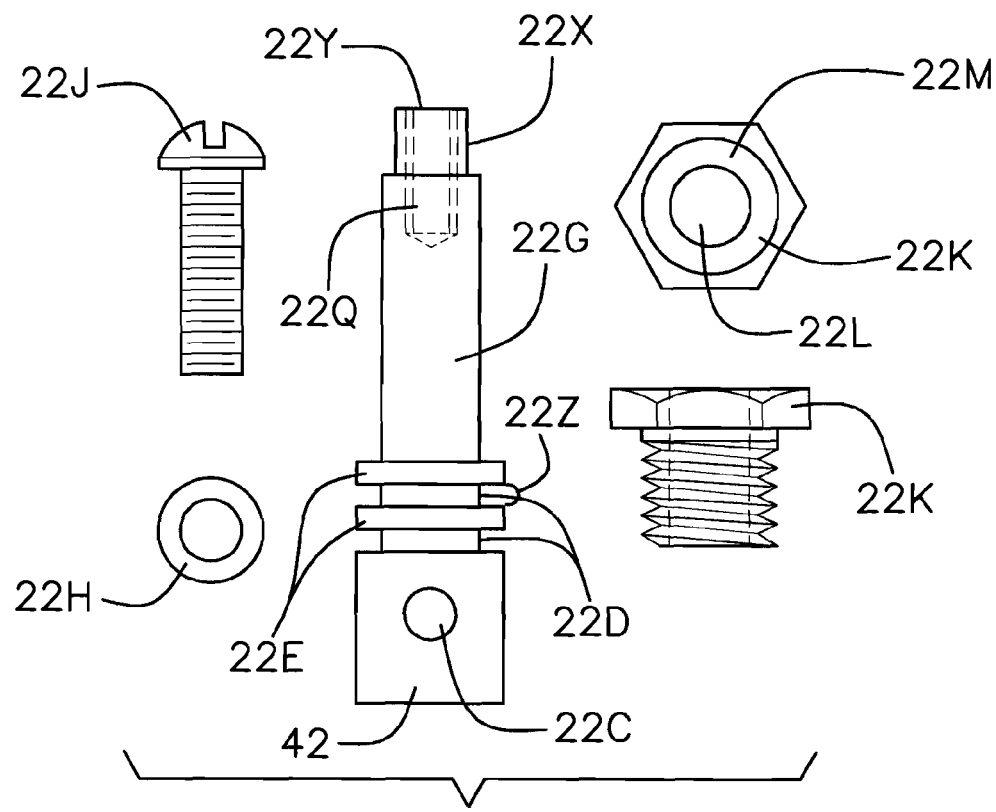
FIG. 9D is a side elevation view of a cylindrical body and its associated components prior to being assembled.

FIGS. 6A-6C highlight the connector body 19, which has three necks 19A of the same diameter and of equal length. Each neck has a number of external threads that allow a number of possible components to overlay a neck 19A and become threadably attached to the connector body 19. The connector body 19 in the device 2 is used in several potential aspects: to connect the coupling 18 to the orifice valve body 20, to connect the nut 13 and the nut 25A to the cold water conduit 14, and to connect the nut 13B and 25B to the hot water conduit 14A. Each of the necks 19A has a bore 19D and has a chamfer 19C. Each of the three threaded ends 19B has a countersink 19E. The connector body 19 has a neck 19A.

Referring in detail to FIGS. 7A-7F of the accompanying drawings, the orifice valve body 20 has an assembly. The function of the orifice valve body 20 and control valve 20C is to open-shutoff water under pressure to the control valve 22A. Control valve 20C has two ends, a first end and a second end, with at least some of the length of the control valve 20C near the first end of the control valve 20C has a diameter very similar to that of bore 20H. The orifice valve body 20 has a central water channel 20N that intersects with bore 20H and travels through the entire orifice valve body 20. Bore 20H is located within orifice valve body 20 and has a diameter. The valve 20C has an attachment 20D, with the attachment 20D being a cylindrical rod that has two ends, a first end and a second end. The first end of the attachment 20D is attached to the second end of the control valve 20C. The attachment 20D has a keyhole 20B on the second end of the attachment 20D, along with an accompanying key 20Y. The attachment 20D has a smaller diameter than that of the control valve 20C. The attachment 20D has a collar 20W, with the collar 20W having a conventional O-ring seal. The attachment ends in a chamfer 20X.

The bore 20H has female threaded section 20S, while the top of the bore 20H has a plane surfacing 20M as shown in the top view 20Q of the orifice valve body 20. Accordingly, the front view of the orifice valve body 20 has a depth of female threaded section 20E and, the male threaded section 20F, with 20F being attached to the neck 20G. The left hand view of the orifice valve body 20 has a female threaded section 20K, a neck 20P, and the chamfer 20J.

Referring to FIGS. 7A-7F again, since all the appropriate parts have been described, it is particularly important to notice that the close tolerance between threaded section 20K and the bore 20H is required. After having the channels 20T and the collar 20W with the conventional O-rings 20U in place, the cylinder 20R is inserted into the bore 20H and fastened with a hexagonal nut 20L which has the same inside diameter as that of the outside diameter of the extended length 20D. The O-rings 20U placed within the channels 20T act as a sealer between the cylinder 20R and the bore 20H, while the O-ring(s) 20U on the collar 20W acts as a rotational seal between the base of the nut 20L and the collar 20W. After opening the water channel 20N with the key 20Y for the orifice 20V, the control valve 22A controls the water pressure to the nipple 23.

FIG. 8 shows the orifice valve body 20 without control valve 20C, although it shows the conduit assembly body 21 in exploded views and also shows the connector body 19 detached from the orifice valve body 20. A length of inflexible tubing 21D having two ends comprising a first end and a second end is used, with the first end of the length of inflexible tubing 21D having a plurality of male threads 21G, which are connected to the female threaded section 20E as shown in FIGS. 7A-7F. The flexible tubing 21A, which has two ends comprising a first end and a second end, has end the first end slid over the tubing 21D such that the first end of the flexible tubing 21A is placed over the first end of the inflexible tubing 21D. Then, a washer 21B goes over the tubing 21D. The hexagonal nut 21C has an inside diameter the same as that of the outside diameter of the flexible tubing 21A. The nut 21C fastens the conduit assembly body 21 to the male threaded end 20P of the orifice valve body 20, as shown in FIGS. 7A-7F. Referring to FIG. 8 again, a washer 21E has a hole with a diameter the same as that of the water channel 20N diameter and an outside diameter the same as that of the inside diameter of the female threaded section 20K. After inserting the washer 21E into the female threaded section 20K, the orifice valve body 20 is connected to the male threaded end 19B at a 90 degree angle to the x-axis of the connector body 19.

Figures 11A, 11B:
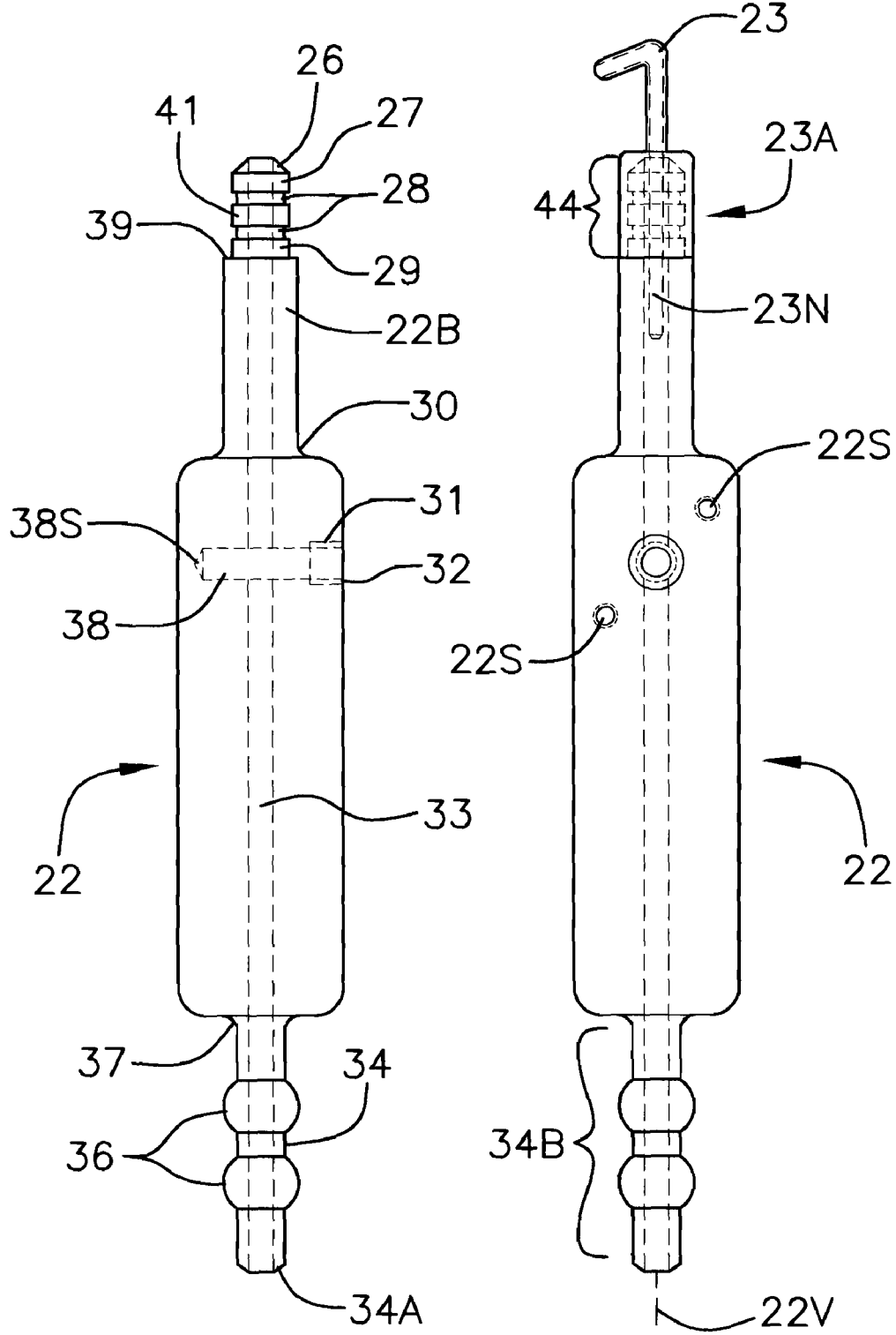
FIG. 11A is a side elevation view of a cylindrical device.
FIG. 11B is a front elevation view of a cylindrical device with an attached nipple assembly.
Figure 12A:
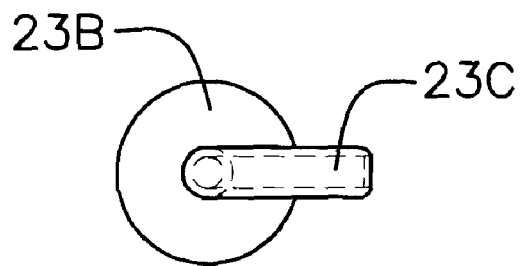
FIG. 12A is a top plan view of a nipple assembly.
Figures 12B, 12C:
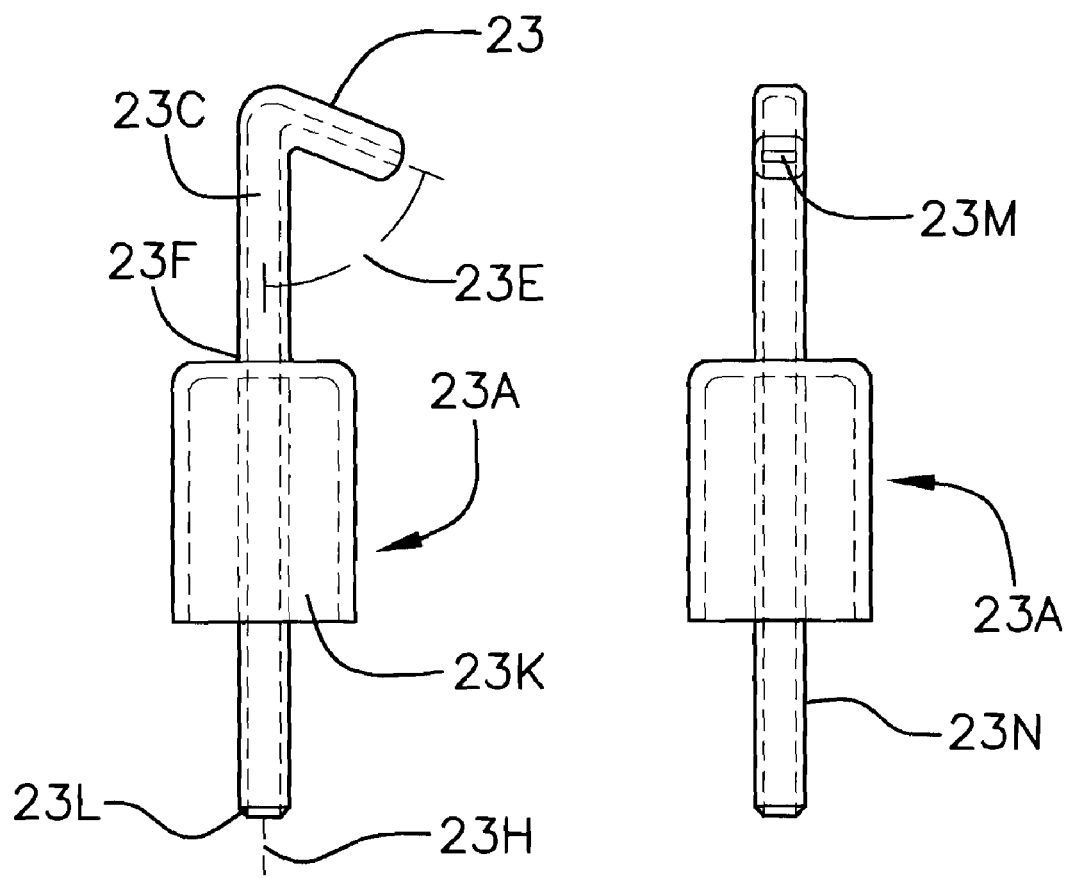
FIG. 12B is a side elevation view of a nipple assembly.
FIG. 12C is a front elevation view of a nipple assembly.

FIGS. 9A-9D show many views of the hand held cylindrical water pressure control valve 22A. The control valve 42 has a diameter and also has two ends comprising a first end and a second end, with the first end of the control valve 42 having an orifice 22C and channels 22D, with the channels having conventional O-rings 20U which act as a sealer between control valve 42 and the bore 38 (as shown in FIGS. 11A-11B). At least some of the length of the control valve 42 near the first end of the control valve 42 has a diameter very similar to that of bore 38. The control valve 42 has shoulders 22E and a collar 22F, with the collar 22F having a conventional O-ring 20U which acts as a rotational seal between the base of a hex nut 22K and the collar 22F. The control valve 42 is also connected to attachment 22G, which is a cylindrical rod having two ends comprising a first end and a second end. The first end of the attachment 22G is attached to the second end of the control valve 42. The hex nut 22K has a bore 22L the same size as that of the diameter of the extended length 22G. The attachment 22G diameter is smaller than that of the control valve 42. The attachment 22G has a bore 22Q, with the bore having a female threaded section 22Y. The hex nut 22K is shown having a spring washer 22M. The female threaded section 22Y of the bore 22Q has a machine screw 22J and also a washer 22H.

Figures 10A, 10B:
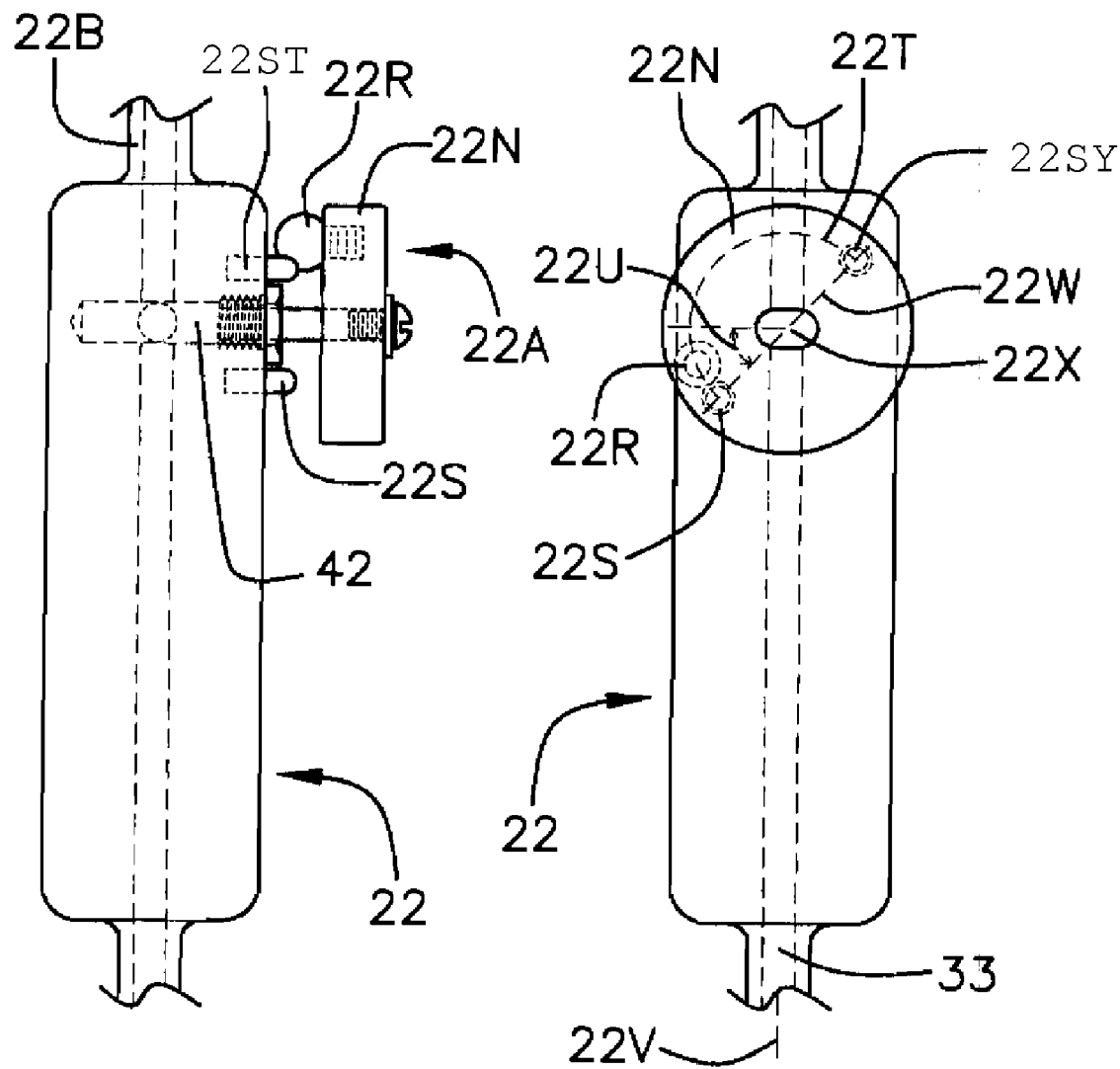
FIG. 10A is a side elevation view illustrating a cylindrical control valve and an associated directional dial.
FIG. 10B is a front elevation view illustrating a cylindrical control valve and an associated directional dial.

The end of the secondary extension 22X has an ellipsoid shape and it has the same depth as that of the thickness of the directional dial 22N. The channels 22D and the collar 22F which are occupied by conventional O-rings 22Z can be inserted into the bore 38, which has a specific diameter, as shown in FIGS. 11A-11B. The hex nut 22K with a spring washer 22M fastens the control valve 22A with female threaded section 31 to the body 22, as shown in FIGS. 11A-11B. The directional dial 22N has a stopper 22R placed on the circumference, as shown in FIGS. 10A-10B. The directional dial 22N with its ellipsoid-shaped hole 22WD slides into the secondary extension 22X of the attachment 22G of the control valve 22A. The machine screw 22J along with the washer 22H fasten the dial 22N to the secondary extension 22X. While tightening hex nut 22K to the control valve 22A, care should be taken to see that the orifice 22C aligns perfectly with the water channel 33 as shown in FIGS. 11A-11B and the control valve 22A rotates freely on the O-ring of the collar 22F.

The constructions and the attachments of the control valve 22A and the directional dial 22N to the body 22 are shown in FIGS. 10A and 10B. In the side view, the body 22 is seen having two stops 22ST. The relative positions of bores 22S and 22SY for the two stops 22ST are seen in detail in the right hand side view and 22S, 22SY are on the straight line 22W going through the center of the control valve 22A and approximately at 55 degree angle 22U with the x-axis of the cylindrical bore 38, as shown in FIGS. 11A-11B. The front view shows the vertical axis 22V going through the center of the water channel 33 and the secondary extension of the cylindrical bore 38. The stopper 22R, the off position 22S, and the on position 22SY are all drawn on a circle that has approximately twice the diameter of the bore 38 and also where water channel 33 crosses bore 38 as a secondary extension 22X. The two stops 22ST are shown in the front sectional view in FIGS. 10A-10B. The stopper 22R at the off position of the directional dial 22N is located on the circumference of the circle, as shown in the front view, and furthermore, the on-position 22RN is shown in the side view. The directional dial 22N is permitted to rotate approximately 90 degrees from stop 22ST to the other stop 22ST. When the stopper 22R on the directional dial 22N is placed against one of the stops 22ST, the orifice on the control valve will be parallel to the water channel located within the hand-held unit (thereby allowing complete water flow within the water channel within the hand-held unit), while when the stopper 22R on the directional dial 22N is placed against the other stop 22ST, the orifice on the control valve will be perpendicular to the water channel located within the hand-held unit (thereby completely preventing water flow within the water channel within the hand-held unit). Obviously, there are an infinite number of positions in between these two endpoints.

FIGS. 11A-11B show the body 22 with the nipple 23. In order to have a general perception of the invention, two important views are shown here. The body 22 has a lower section 34B and that section has a chamfer 34A, beads or small ball-shaped body or projecting rims bands 36, a bead gap 34 and a neck 37. The tubing 21A of the conduit assembly body 21 slides over the section 34B up to the neck 37. A pressure clamp over the gap 34 may be necessary to have a tight connection. In the front view of the body 22, it shows the water channel 33 runs end to end within the body 22 and intersects with the bore 38. In the side view of the body 22, the bore 38 has a space between the body 22 and the chamfer 38S of the bore. The bore 38 has a female threaded section 31, with an approximate depth for the hex nut 22K. The plane surfacing 32 allows for surface-to-surface sealing of the hex nut 22K. The upper section of the body 22 has a neck 30, with the neck 30 having an upper neck section 22B. The end of the upper neck section 22B has a collar 39 on which the nipple body 23A rotates at 360 degrees. The upper neck section 22B had channels 28, with the channels having conventional O-rings. The channels also are located adjacent to shoulders 27, 29 and 41, with shoulder 27 having chamfer 26. Referring to FIGS. 11A-11B again, the right-hand side view shows female threaded locations 22S and 22SY for the stop studs 22ST. Upper section 44, attached to collar 39, has an attachable nipple body 23A which rotates 360 degrees on the collar 39. The nipple body 23A includes a nipple 23 with a slit 23M powered by the water energy from the domestic water supply line, which is preferably approximately 20 psi. However, the speed and pressure of the water exiting the slit 23M can be controlled by the control valve 22A of the body 22.

Referring now specifically to FIGS. 11A-12C, the separate nipple bodies 23A can be inserted or attached to the upper section 44 for each person within a particular group or family. The nipple has a razor sharp slit 23M with the slit 23M being connected to the internal water channel 23C. The slit has an angle 23E of approximately 70 degrees with the x- and y-coordinates of the slit 23M. The extended section 23N of the small cylindrical tubing of the nipple 23 is to be inserted into the hand-held cylindrical control device section 44 through the water channel 33 until the nipple body 23A rotates on the collar 39 as shown in FIGS. 11A-11B. Two conventional O-rings located within the channels 28 seal the hollow housing 23K and at the same time allow the nipple body 23A on the collar 39 to freely rotate on a 360-degree axis. The nipple body 23A has a neck 23F, a chamfer 23L and a vertical axis 23H.

After completing the connections and the attachments of all described parts herein and mentioned in FIGS. 1 through 12C, the dental hygiene pulsatory slit apparatus is ready for the dental hygiene use for the entire family.

As previously stated, an important part of the invented device is that it can be connected to a valve or valves of the water supply lines under a sink in the bathroom. It is simple when the sink is having no enclosures, because the water carrying flexible tubing 21A can go around the sink. When the sink is enclosed with a cabinet or has a marble top over the sink, the flexible tubing can be threaded through a small bore of the enclosed cabinet or of the marble top of the sink. The bore has to be made particularly for the use of the invented dental hygiene device. For the life long use of the device, it is a very small price to pay. When building a new home or remodeling a bathroom, it is easy to install this device permanently for the benefits of the oral health of the entire family.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What I claim as my invention is:

1. An oral hygiene device in combination with an existing plumbing system, the oral hygiene device comprising:
    (a) a connector body,
    (b) means for attaching the connector body to an incoming water line comprising at least one coupling, wherein the coupling is connected to the connector body and the coupling is connected to the incoming water line,
    (c) an open-shutoff orifice valve body attached to the connector body, wherein the orifice valve body further comprises:
        (i) a bored hole located within the orifice valve body, the bored hole having a diameter,
        (ii) a control valve having two ends, comprising a first end and a second end, the control valve having a diameter, wherein some of the length of the control valve near the first end of the control valve has a diameter very similar to the diameter of the bored hole,
        (iii) a water channel located within the orifice valve body, the water channel intersecting with the bored hole, the water channel passing through the entire orifice valve body,
        (iv) a cylindrical attachment having two ends, a first end and a second end, the first end of the cylindrical attachment being attached to the second end of the control valve,
        (v) an orifice located on the control valve near the first end of the control valve,
        (vi) wherein the first end of the control valve is inserted into the bored hole to the point where the orifice bisects the water channel, and
        (vii) means for adjusting the position of the control valve in relation to the orifice valve body to allow or disallow water to pass through the water channel located within the orifice valve body,
    (d) a conduit assembly body attached to the orifice valve body,
    (e) a hand-held unit, the hand-held unit comprising a cylindrical body,
    (f) means for attaching the hand-held unit to the conduit assembly body,
    (g) means for expelling the water out of the hand-held unit, and
    (h) means for controlling the amount of water being emitted through the hand-held unit.

2. An oral hygiene device according to claim 1 wherein the means for adjusting the position of the control valve in relation to the orifice valve body to allow or disallow water to pass through the water channel located within the orifice valve body further comprises:
    (a) a keyhole located on the cylindrical attachment near the second end of the cylindrical attachment,
    (b) a key,
    (c) wherein the key can be inserted into the keyhole and used to rotate the cylindrical attachment, thereby rotating the control valve, thereby allowing water to flow or not flow through the orifice in the control valve at varying flow rates.

3. An oral hygiene device according to claim 1 wherein the means for attaching the hand-held unit to the conduit assembly body further comprises:
    (a) a plurality of internal threads located on the orifice valve body,
    (b) a length of inflexible tubing, the length of inflexible tubing having two ends comprising a first end and a second end,
    (c) a plurality of external threads located on the first end of the length of inflexible tubing,
    (d) a length of flexible tubing, the length of flexible tubing having two ends comprising a first end and a second end,
    (e) wherein the plurality of external threads located on the first end of the length of inflexible tubing is threadably connected to the plurality of internal threads located on the orifice valve body,
    (f) further wherein the length of flexible tubing is slid over the length of inflexible tubing such that the first end of the length of flexible tubing overlaps the first end of the length of inflexible tubing, and (g) further wherein the second end of the length of flexible tubing is attached to the hand-held unit.

4. An oral hygiene device according to claim 3 wherein the means for controlling the amount of water being emitted through the hand-held unit further comprises:
   (a) a bored hole located within the hand-held unit, the bored hole having a diameter,
   (b) a water channel located within the hand-held unit, the water channel intersecting with the bored hole, the water channel passing through the entire hand-held unit,
   (c) a control valve having two ends, comprising a first end and a second end, the control valve having a diameter, wherein some of the length of the control valve near the first end of the control valve has a diameter very similar to the diameter of the bored hole,
   (d) a cylindrical attachment having two ends, a first end and a second end, the first end of the cylindrical attachment being attached to the second end of the control valve,
   (e) an orifice located on the control valve near the first end of the control valve,
   (f) wherein the first end of the control valve is inserted into the bored hole in the hand-held unit to the point where the orifice bisects the water channel,
   (g) means for adjusting the position of the control valve in relation to the hand-held unit to allow or disallow water to pass through the water channel located within the hand-held unit.

5. An oral hygiene device according to claim 4 wherein the means for adjusting the position of the control valve in relation to the hand-held unit to allow or disallow water to pass through the water channel located within the hand-held unit further comprises:
   (a) a directional dial,
   (b) means for attaching the directional dial to the second end of the cylindrical attachment attached to the control valve associated with the hand-held unit,
   (c) means for allowing the directional dial to rotate the control valve in between a position in which the orifice on the control valve is parallel with the water channel located within the hand-held unit and a position in which the orifice on the control valve is perpendicular with the water channel located within the hand-held unit.

6. An oral hygiene device according to claim 5 wherein the means for allowing the directional dial to rotate control valve in between a position in which the orifice on the cylindrical rod is parallel with the water channel located within the hand-held unit and a position in which the orifice on the control valve is perpendicular with the water channel located within the hand-held unit further comprises:
   (a) a stopper attached to the directional dial,
   (b) a pair of stops inserted into the hand-held unit,
   (c) wherein the pair of stops are positioned on the hand-held unit such that the stopper attached to the directional dial will come into contact with each of them, and
   (d) further wherein the positioning of the pair of stops will allow the directional dial to rotate approximately 90 degrees, and
   (e) further wherein when the stopper attached to the directional dial is placed against one of the pair of stops, the orifice on the control valve is parallel with the water channel located within the hand-held unit, and further wherein when the stopper attached to the directional dial is placed against the remaining stop of the pair of stops, the orifice on the control valve is perpendicular with the water channel located within the hand-held unit.

7. An oral hygiene device according to claim 1 wherein the means for expelling the water out of the hand-held unit further comprises a nipple, the nipple being attached to the hand-held unit.

8. An oral hygiene device according to claim 7 wherein the nipple further comprises:
   (a) a nipple body, the nipple body including a housing,
   (b) a water channel located within the nipple body, and
   (c) a slit attached to an end of the water channel.

* * * * *